(12) United States Patent
Smith

(10) Patent No.: US 7,132,657 B2
(45) Date of Patent: Nov. 7, 2006

(54) INFRARED GAS DETECTOR

(75) Inventor: Patrick G. Smith, Shakopee, MN (US)

(73) Assignee: Sensor Electronics Corporation, Minneapolis, MN (US)

( * ) Notice: Subject to any disclaimer, the term of this patent is extended or adjusted under 35 U.S.C. 154(b) by 207 days.

(21) Appl. No.: 10/774,910

(22) Filed: Feb. 9, 2004

(65) Prior Publication Data
US 2005/0173635 A1    Aug. 11, 2005

(51) Int. Cl.
G01J 5/02       (2006.01)
G01N 21/35    (2006.01)
G01N 21/61    (2006.01)

(52) U.S. Cl. .............. 250/339.13; 250/343; 356/437; 73/23.2

(58) Field of Classification Search ............ 250/339.1, 250/339.13, 344, 345; 356/437
See application file for complete search history.

(56) References Cited

U.S. PATENT DOCUMENTS

| | | |
|---|---|---|
| 2,269,674 A | 1/1942 | Liddel et al. |
| 2,431,019 A | 11/1947 | Barnes |
| 2,806,144 A | 9/1957 | Berger et al. |
| 2,866,900 A * | 12/1958 | Busignies et al. .......... 250/343 |
| 2,963,580 A | 12/1960 | Smart |
| 3,364,351 A | 1/1968 | Palmer et al. |
| 3,405,268 A | 10/1968 | Brunton |
| 3,696,247 A | 10/1972 | McIntosh et al. |
| 3,898,462 A | 8/1975 | Ichida et al. |
| 3,932,754 A | 1/1976 | Riedl et al. |
| 4,278,538 A * | 7/1981 | Lawrence et al. .......... 250/226 |
| 4,336,453 A | 6/1982 | Imaki et al. |
| 4,480,191 A | 10/1984 | Karpowycz |
| 4,632,563 A | 12/1986 | Lord, III |
| 4,746,218 A | 5/1988 | Lord, III |
| 4,772,790 A | 9/1988 | Aldridge |
| 4,874,572 A | 10/1989 | Nelson et al. |
| 5,015,099 A | 5/1991 | Nagai et al. |
| 5,095,913 A | 3/1992 | Yelderman et al. |
| 5,210,702 A | 5/1993 | Bishop et al. |
| 5,252,828 A | 10/1993 | Kert et al. |
| 5,281,816 A | 1/1994 | Jacobson et al. |
| 5,319,199 A | 6/1994 | Stedman et al. |
| 5,343,043 A | 8/1994 | Johnson |
| 5,371,367 A | 12/1994 | DiDomenico et al. |
| 5,401,967 A | 3/1995 | Stedman et al. |
| 5,418,366 A | 5/1995 | Rubin et al. |
| 5,429,805 A * | 7/1995 | Uno et al. .................... 422/83 |
| 5,489,777 A | 2/1996 | Stedman et al. |

(Continued)

OTHER PUBLICATIONS

Patrick G. Smith, "Continuous Monitoring of EtO Concentrations during Sterilization," *Medical Device & Diagnostic Industry*, Feb. 2001, pp. 81, 82, 84-86, Canon Communications, Los Angeles, CA.

(Continued)

*Primary Examiner*—David Porta
*Assistant Examiner*—Frederick F. Rosenberger
(74) *Attorney, Agent, or Firm*—Allison Johnson

(57) ABSTRACT

A gas detector that includes at least one source of infrared radiation, at least two analytical detectors, each analytical detector adapted to provide an output signal indicative of a first gas of interest and positioned to receive radiation from the source of radiation, at least one reference detector adapted to receive radiation of a predetermined wavelength, a sample chamber for receiving a gaseous sample, and an optical path length disposed between the source of radiation and the analytical detectors and passing through the sample chamber.

43 Claims, 4 Drawing Sheets

U.S. PATENT DOCUMENTS

| | | | |
|---|---|---|---|
| 5,498,872 A | 3/1996 | Stedman et al. | |
| 5,515,859 A | 5/1996 | Paz | |
| 5,585,636 A | 12/1996 | Dollansky | |
| 5,591,975 A | 1/1997 | Jack et al. | |
| 5,650,624 A * | 7/1997 | Wong | 250/338.5 |
| 5,721,430 A | 2/1998 | Wong | |
| 5,726,450 A | 3/1998 | Peterson et al. | |
| 5,797,682 A | 8/1998 | Kert et al. | |
| 5,886,348 A * | 3/1999 | Lessure et al. | 250/339.13 |
| 5,898,183 A * | 4/1999 | Teder | 250/341.8 |
| 6,061,141 A * | 5/2000 | Goldenberg et al. | 356/437 |
| 6,277,081 B1 | 8/2001 | Susi et al. | |
| 6,392,234 B1 | 5/2002 | Diekmann | |
| 6,414,310 B1 | 7/2002 | Smith | |
| 6,545,278 B1 | 4/2003 | Mottier et al. | |
| 6,555,820 B1 * | 4/2003 | Tacke et al. | 250/339.13 |
| 6,580,934 B1 | 6/2003 | Braig et al. | |
| 6,875,399 B1 * | 4/2005 | McVey | 250/339.13 |
| 2002/0011568 A1 | 1/2002 | Diekmann | |
| 2003/0015019 A1 | 1/2003 | O'Brien | |

OTHER PUBLICATIONS

Sensor Electronics Corporation Infrared Gas Detection Instruction Manual, (28 pages), Sensor Electronics Corporation, Minneapolis, MN.

Sensor Electronics Corporation EtO SIGNATURE Ethylene Oxide Monitor product literature, (4 pages), Sensor Electronics Corporation, Minneapolis, MN.

Sensor Electronics Corporation SEC SIGNATURE Process Gas Analyzer Product literature, (2 pages), (Jul. 2003) Sensor Electronics Corporation, Minneapolis, MN.

Sensor Electronics Corporation SEC MILLENIUM Infrared Hydrocarbon Gas Detector product literature, (2 pages), (Mar. 2003) Sensor Electronics Corporationm, Minneapolis, MN.

* cited by examiner

INFRARED GAS DETECTOR

BACKGROUND

The present invention relates to increasing the sensitivity of a gas detector.

There is an unending need to improve the sensitivity of analytical methods and apparatus. In the field of gas detection, for example, improving sensitivity can improve accuracy, the ability to detect trace amounts of a gas, the safety of a system, and process quality.

Gas detectors are often used to detect a gas of interest under various conditions and in a variety of environments. Many times it is also necessary to continuously monitor for the presence and amount of a gas in an environment. Often it is desirable that the detector measure the concentration of a gas in an accurate and timely manner Gas detectors often include a source of radiation, a sample chamber and a detector. Various attempts have been made to increase the sensitivity of gas detectors including increasing the distance between the source of radiation and the detector, which distance is referred to as the "optical path length." Increasing this distance can increase the amount of sample measured, and therefore the sensitivity of the analysis. Theoretically, a larger sample volume will contain a larger number of gas particles, which in turn can increase the sensitivity of the detector.

One way in which the optical path length has been increased has been through the use of reflective mirrors. The use of mirrors can be undesirable, however, because mirrors tend to corrode and accumulate residue over time. As the residue builds up, the amount of radiation reflected from the mirror decreases, which contributes to a decrease in the useful life of the detector. This is particularly true when vapors, such as water vapors, are present in the sample being measured.

Others have attempted to increase the optical path length by physically increasing the length of the sample chamber, which tends to increase the length of the apparatus as a whole. In addition to undesirably increasing the overall bulk of the apparatus, such an arrangement tends to increase the radiation scattering due to the increased distance between the excitation source and the detector.

Increasing the length of the optical path in a gas detector does not necessarily provide a corresponding increase in the amount of energy capable of being measured. To the contrary, increasing the path length often results in diminishing returns in terms of energy. FIG. 1 illustrates the relationship between optical path length and absorption. The increase in absorbance is exponential relative to an increase in optical path length. As the optical path length gets larger, an incremental increase in path length provides a relatively small increase in absorbance, rendering the increase in path length less efficient in terms of absorption. Thus, incrementally increasing the optical path length of the detector becomes an increasingly less efficient means for increasing the amount of measurable energy.

Methods and apparatus for improving the sensitivity of gas detectors are needed. Increasing the sample size and hence sensitivity of gas detectors is particularly desired, particularly where it is desirable to quantify the concentration of the gas of interest.

SUMMARY

In one aspect, the invention features a gas detector that includes at least one source of infrared radiation; at least two analytical detectors, each analytical detector adapted to provide an output signal indicative of a first gas of interest, the analytical detectors being positioned to receive radiation from the source of radiation, at least one reference detector adapted to provide an output signal independent of the first gas of interest; and a sample chamber for receiving a gaseous sample, the optical path from the source of infrared radiation to the analytical detectors passing through the sample chamber.

In one embodiment, the detector further includes a means for summing the signal detected by the two analytical detectors. In some embodiments, the analytical detectors further include the means for summing. In other embodiments, the summing means includes a summing amplifier. In another embodiment, the summing means includes a summing node. In another embodiment, the summing means includes an analog summing node. In another embodiment, the summing means includes a digital summing node. In one embodiment, the summing means includes a microprocessor.

In other embodiments, the detector further includes an interference filter positioned to filter radiation received by at least one of the analytical detectors.

In another embodiment, the source of infrared radiation includes at least one of heated filament, a black body source, and light emitting diode. In one embodiment, the source of infrared radiation includes an incandescent lamp. In other embodiments, the source of infrared radiation consists of one source of infrared radiation.

In some embodiments, the detector includes at least three analytical detectors. In other embodiments, the detector includes at least four analytical detectors. In one embodiment, the detector further includes at least two additional analytical detectors, the at least two additional analytical detectors adapted to provide an output signal indicative of a second gas of interest, the second gas of interest being different from the first gas of interest.

In another embodiment, the detector includes a filter interposed between the at least one source of infrared radiation and each analytical detector, the filter being adapted to transmit infrared radiation of a first band of wavelengths, the first band of wavelengths corresponding to radiation of a wavelength absorbed by a first gas of interest. In one embodiment, a filter is interposed between the at least one source of infrared radiation and each additional analytical detector, the filter being adapted to transmit radiation of a second band of wavelengths, the second band of wavelengths corresponding to radiation of a wavelength absorbed by a second gas of interest. In another embodiment, a filter is interposed between the at least one source of infrared radiation and each reference detector, each filter being adapted to transmit radiation of a third band of wavelengths, the third band of wavelengths corresponding to radiation of a wavelength that is not absorbed by a first gas of interest and a second gas of interest.

In some embodiments, the detector further includes a microprocessor for receiving and analyzing signals generated by the analytical detectors.

In another aspect, the invention features a gas detector for detecting a predetermined gas, the gas detector includes a source of infrared radiation, and a plurality of infrared radiation detectors, at least two of the infrared radiation detectors being adapted to detect radiation of a first wavelength and being adapted to provide an output signal corresponding to the presence of the gas of interest. In one embodiment, the gas detector further includes a means for summing signals generated by the analytical detectors.

In other aspects, the invention features a method of detecting gas using a gas detector that includes a source of infrared radiation, at least two analytical detectors, each of the at least two analytical detectors being adapted to generate a signal indicative of a first gas of interest, a sample chamber, and an optical path passing through the sample chamber, the method including, transmitting infrared radiation from the source of infrared radiation through a gaseous sample present in the sample chamber of the gas detector, detecting infrared radiation of a predetermined wavelength at the analytical detectors, sending a signal from the analytical detectors to a processor; and summing the signals from the analytical detectors. In one embodiment, the summing occurs in the analytical detectors. In other embodiments, the summing occurs in a processor. In another embodiment, the summing occurs prior to the analytical detectors sending a signal to the processor. In other embodiments, the summing occurs after the analytical detectors send a signal to the processor.

In some embodiments, radiation from the source of infrared radiation that is incident on the analytical detectors is essentially unreflected from surfaces interposed between the analytical detectors and the source of infrared radiation.

In another aspect, the invention features a method of analyzing a gaseous sample, the method including passing the gaseous sample through the sample chamber of a gas detector that includes at least one source of infrared radiation, at least two analytical detectors, each analytical detector being adapted to provide an output signal indicative of a first gas of interest, the analytical detectors being positioned to receive radiation from the source of radiation, and a sample chamber, radiating the gaseous sample with radiation from the source of infrared radiation, detecting the radiation at the analytical detectors, generating signals corresponding to the detected radiation, summing signals generated by the analytical detectors, and analyzing the signals generated by the detectors.

In one embodiment, the analyzing includes determining the presence or absence of a first gas of interest in the gaseous sample. In other embodiments, the analyzing includes determining the concentration of a first gas of interest in the gaseous sample. In some embodiments, the analyzing includes determining the concentration of the first gas of interest, and determining the concentration of a second gas of interest.

The present invention provides a robust gas detector that includes at least two analytical detectors for detecting a gas of interest. The gas detector can be configured to sum the signals generated by the analytical detectors, which provides a detector with enhanced sensitivity relative to a detector that includes a single detector for the gas of interest.

Figure 1:
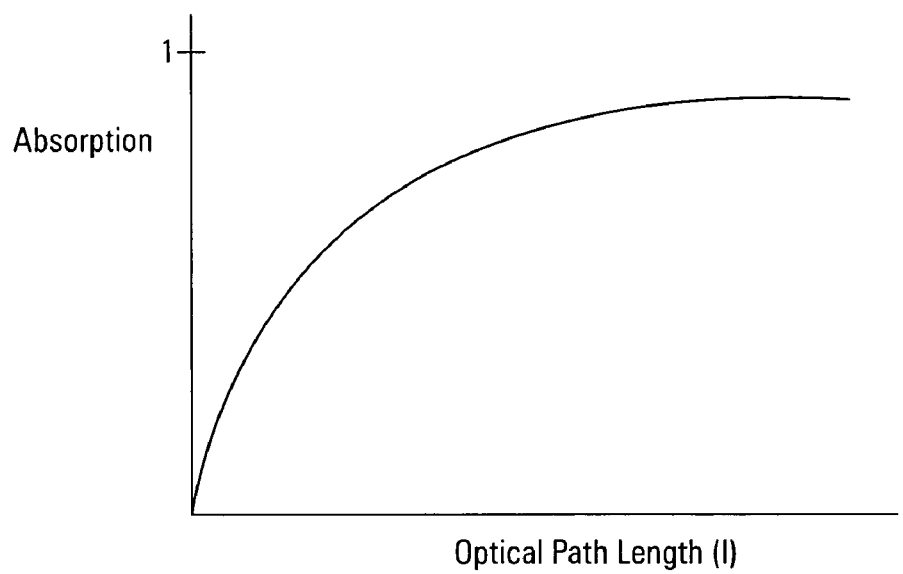
FIG. 1 is a graphical representation of infrared radiation absorption by a gas versus the path length over which that absorption is measured.

Other features and advantages will be apparent from the following description of the preferred embodiments and from the claims.

DETAILED DESCRIPTION

The gas detector includes a source of infrared radiation, a sample chamber, at least two analytical detectors for detecting a gas of interest and optionally at least one reference detector. In operation, a gaseous sample passes through the sample chamber of the gas detector, infrared radiation is transmitted through the gaseous sample, and the analytical detectors detect for the presence of at least one gas of interest in the sample. In preferred embodiments, the gas detector includes summing nodes that sum the signals generated by the analytical detectors. The amount of infrared radiation received by the detectors is used to determine the presence, absence, amount, or a combination thereof, of at least one predetermined gas in a gaseous sample.

The source of infrared radiation (IR) is positioned such that the analytical and reference detectors receive the radiation emitted from the radiation source. Preferably the source of infrared radiation is disposed relative to the analytical and reference detectors such that the radiation travels along a continuous linear path to the detectors. The source of infrared radiation can be any source of infrared radiation capable of emitting a sufficient amount of infrared radiation for detection by the analytical and reference detectors. Useful sources of infrared radiation emit radiation include sources that emit in the near IR, mid IR and far IR including radiation from about 750 nanometers (i.e., just longer than red in the visible spectrum) to 1 millimeter (i.e., on the border of the microwave region), at least about 2 $\mu$m, or even from 2 $\mu$m to 4 $\mu$m. The source of infrared radiation can also emit radiation having a wavelength outside of the infrared spectrum. Suitable infrared radiation sources include, e.g., black bodies (e.g., heated filaments (e.g., incandescent lamps and micro-machined, heated metal filaments)), light emitting diodes, laser diodes, and combinations thereof. Useful metals for the heated filaments include, e.g., tungsten and alloys of nickel, chromium, iron, and combinations thereof. A wide variety of commercially available infrared excitation sources are suitable including, e.g., Ion Optics (Waltham, Mass.). The source of infrared radiation can include a combination of one or more sources of infrared radiation. Preferably, for ease of manufacture and use, a single infrared radiation source is utilized.

The term "channel" as used herein refers to a detector that is positioned to receive light transmitted from a light source and through a sample volume of gas, and configured to receive a wavelength or band of wavelengths of the light. In the case where the detector is an analytical detector, the channel is referred to as an "analytical channel." In the case where the detector is a reference detector, the channel is referred to as a "reference channel." For ease of manufacture and use, it is preferred that the gas detector includes substantially identical analytical channels such that the light received by the detectors of the analytical channels has passed through essentially the same sample. It is also preferred that gas detectors have substantially identical reference channels. Further, it is preferred that the analytical and reference channels are substantially identical, such that reference detector receives infrared radiation transmitted through essentially the same gaseous sample and optical path as the infrared radiation incident on the analytical detector for which it is a reference.

The sample chamber is a volume along the optical path through which a gas is allowed to pass (e.g., by diffusion, flow, turbulence or a combination thereof). The sample chamber can be defined by walls. In other embodiments, the sample chamber does not necessarily include walls or any physical structure defining the chamber.

The optical path is the path along which radiation travels from the source of infrared radiation to the detectors. The length of the optical path, i.e., the distance between the infrared radiation source and the analytical and reference detectors, preferably falls in the range of path lengths within which the curve that represents the relationship between path length and absorption has the greatest slope. Any optical path length can be used. One example of a useful range of optical path lengths is from about 1 centimeters (cm) to about 25 cm.

The analytical detectors preferably are optically balanced such that when radiation incident thereon is shifted in some manner, the sum of the radiation received at each type of detector provides accurate information about the gaseous sample present in the sample chamber.

The analytical detectors are adapted to detect radiation of a predetermined band of wavelengths. The wavelength band is predetermined based on the type and concentration of gas or gases of interest. The wavelengths that are transmitted to the analytical detector are essentially only those wavelengths absorbed by a gas of interest. Preferably, the gas detector is configured such that each analytical detector receives a band (i.e., 0.05 µm to 4 µm) of wavelengths, or even a single wavelength, of infrared radiation, even when a particular gas of interest is capable of absorbing such radiation at multiple wavelengths.

The wavelength band transmitted to the analytical detector is selected based on the components anticipated to be present in a gaseous sample and the particular gases of interest. Useful wavelength bands include those wavelengths absorbed by gases including, e.g., gases that include a carbon hydrogen bond (e.g., hydrocarbon gases (e.g., methane, ethane, propane and butane)), vapors of compounds that include a carbon hydrogen bond (e.g., butane, pentane, hexane, heptane, octane, and nonane), carbon dioxide, carbon monoxide, nitrous oxide, and water vapor. When detection of a gas or vapors that includes a carbon hydrogen bond is desired, the analytical detectors of the system can be configured to detect infrared radiation centered at a wavelength of from about 3.3 µm to 3.4 µm. Likewise analytical detectors can be configured to detect infrared radiation of a wavelength centered at from about 2.4 µm to about 2.9 µm, or even about 2.69 µm, for water vapor, about 4.27 µm for carbon dioxide, about 4.77 µm for carbon monoxide, and about 2.85 µm for nitrous oxide.

The analytical detectors can be adapted to detect at a predetermined band of wavelengths through the use of band pass filters including, e.g., interference filters. Useful band pass filters include thin sheets of at least one filter material including, e.g., silicon, quartz, germanium and potassium bromide. Preferred filters include multiple layers of filter materials, including multiple layers of different filter materials.

The gas detector can include multiple sets of multiple analytical detectors. Each set of analytical detectors can be adapted to detect radiation of a predetermined band of wavelengths. The predetermined band of wavelengths can be the same or different for each set of detectors. Different sets of analytical detectors can be used to detect a different gas of interest.

The reference detector is adapted to detect infrared radiation of a wavelength that is different from the wavelength of radiation detected by to the analytical detectors. The reference detector is adapted to detect infrared radiation of a wavelength that is not affected by the gaseous sample (i.e., the gaseous sample does not absorb in the wavelength or band of wavelengths transmitted to the reference detector) or the concentration of the gas(s) present in the gaseous sample. To achieve this effect, a wavelength discriminating component, preferably a bandwidth filter, is interposed between the source of radiation and the reference detector. The filter can be positioned before or after the infrared radiation enters or exits the gaseous sample. For simplicity of design, it is preferred to include a filter positioned downstream of the gaseous sample. The filter is configured and selected to allow passage of radiation of a predetermined band of wavelengths of radiation to the reference detector and to inhibit, and preferably prevent, radiation of other wavelengths from reaching the reference detector. Preferably the midpoint of the spectrum that is allowed to pass through the filter is defined by the wavelength that is not absorbed by the gas of interest plus or minus from 0.05 µm to 4.0 µm. Particularly useful reference detectors include those configured to detect wavelengths from 3.8 µm to 4.0 µm, or even from 2.9 µm to 3.1 µm.

Any suitable infrared detector may be used for the analytical and reference detectors. Useful detectors include, e.g., thermopiles, photoresistors, photoconductors, photodiodes (e.g., photovoltaic cells and photoconductors), pyroelectric detectors, and combinations thereof. A wide variety of suitable infrared detectors are commercially available including, e.g., thermopiles from Perkin Elmer (Wellesley, Mass.) and Dexter Research Center Inc. (Dexter, Mich.).

While each infrared detector need not be identical, for ease of manufacture and use, in preferred embodiments the infrared detectors are essentially the same. If the individual detectors are not of the same type or otherwise differ in their configuration, adjustments may need to be made in the output circuitry associated with the gas detector. Those of ordinary skill in the art can recognize the need or desire for and make such modifications as warranted.

Each detector generates a signal (e.g., a voltage) corresponding to the amount of energy, I, (i.e., infrared radiation) received thereby. The amount of energy, I, (i.e., radiation) received by the detectors is influenced by the gas(es) present in the optical path and the length of the optical path, l. The amount of energy is calculated as follows:

$$I = I_o e^{-\gamma l c}$$

where $I_o$ is the initial amount of energy emitted by the source of radiation, $\gamma$ is the absorption constant of the gas of interest, and c is the concentration of the gas of interest.

In a preferred embodiment, the signals from the analytical detectors for a single gas of interest are summed. By summing the signals, the signal indicative of the detected gas is enhanced.

The present inventor has discovered that a gas detector configuration that has an optical path, l, includes "n" analytical detectors for a single gas of interest, where $n \geq 2$, and provides an output signal consisting of the sum of the signals of the n analytical detectors obtained for a single gas of interest, provides an exponential increase in sensitivity relative to a gas detector having a single analytical detector for each gas of interest and an optical path length, L, where L is "n" times "l" (i.e., L=n*l) where "n" is a path length multiplier and is equal to the n set forth above and "l" is the length of the optical path set forth above.

The present gas detector configuration, in which there are multiple analytical channels configured to detect the same predetermined wavelength or band of wavelengths, provides a sensitivity multiplier "R" relative to the traditional method of increasing the sensitivity of a gas detector, i.e., physically increasing the length of the optical path "L" or using reflective surfaces to increase the length of the optical path.

The relationship, which is referred to herein as the sensitivity multiplier, R, between the change in sensitivity achieved by the present invention relative to the change in sensitivity achieved by traditional methods of increasing sensitivity is derived as follows.

In the traditional method of increasing sensitivity, when the path length l is increased by a factor of n, the sensitivity increase is represented by the following equation:

$$I_1 = I_o e^{-\gamma c n l}.$$

where $I_1$ is the intensity received by the detector of a traditional system, $I_o$, $\gamma$, c, n and l are as described above.

In the present invention, when the gas detector includes n detectors are for a single gas of interest, the increase in the sensitivity of the system is represented by the following equation $$I_2 = n I_o e^{-\gamma c l}.$$

where $I_2$ is the intensity received by the detectors and n, $I_o$, $\gamma$, c, and l are as described above.

Accordingly, the sensitivity multiplier, R, is the relationship of $I_2/I_1$, which is expressed as follows $$R = n \cdot e^{-\gamma c (l - l/n)}$$

where n, l, $\gamma$, and c are as defined above. Thus, when the gas detector includes two analytical detectors for measuring the energy transmitted through a gaseous sample at a single predetermined wavelength, for example, and whose outputs are summed, the amount of energy measured and the corresponding increase in sensitivity of the gas detector having a physical optical path length l is as follows:

$$I = 2 I_o e^{-\gamma (1/2) c}$$

which results in more than twice the sensitivity relative to a single channel having an effective path length of 2l.

In other words, by measuring over the same path length simultaneously with multiple independent channels and summing the outputs generated by the detectors of those channels, sensitivity can be increased tens or even hundreds of times relative to traditional methods of using a single channel and increasing the path length in a linear fashion or by using reflective surfaces. As a result, a potentially very sensitive device can be provided in a relatively small package without the need for path length enhancing devices such as mirrors.

Summing the signal can also minimize or effectively eliminate the error and noise present in the signal. Sources of error include variations in the amount of radiation incident on each analytical and reference detector due to positioning of the individual analytical detectors, reference detectors, the source of radiation or a combination thereof. By increasing the number of signals measured and calculated, the electrical signal noise that is inherently present in the system is minimized, or even essentially eliminated.

The signals generated by the detectors can be summed using any suitable device including, e.g., an analog device. Alternatively or in addition, the signals generated by the detectors can be routed to a microprocessor, or other tool suitable for processing the signals, and summed by the processor.

The frequency with which signals are generated by the detectors and/or collected by the signal processor are based upon a desired sampling frequency. Although any suitable and desirable sampling frequency may be used, preferably data is sampled at least once per second in order to promote continuous and effective monitoring of a gaseous sample.

The signals are routed to a microprocessor or other tool suitable for analyzing and processing the signals into one or more outputs (e.g., information) desired by a user of the gas detector apparatus. The signals generated by the detectors can be used to determine the presence, absence, or concentration of the gas of interest, and combinations thereof. One method of analyzing the signals generated by the detectors is by comparing the sum of the signals generated by the analytical detectors to the sum of the signals generated by the reference detectors. Alternatively, signals received from each analytical detector associated with a particular gas of interest can be compared with the signal received from a corresponding reference detector. An automatic control circuit useful for this purpose is described, for example, in U.S. Pat. No. 6,414,310, assigned to Sensor Electronics Corporation.

If desired, and depending on the type of analytical tool used, a signal amplifier may be used to enhance the signals generated by the detectors. Further, converters (e.g., analog-to-digital) and the like may be used to effectively couple the infrared radiation detectors to an analytical tool (e.g., a microprocessor).

Information related to the detected signals can be displayed on any suitable display including, e.g., an LED display, monitor, computer screen, video screen, hand-held devices (e.g., palm display devices (e.g., personal digital assistant), telephones and pagers), and chart recorders. The information provided by the display can be provided in the form of a digital display on the device, itself, a remote display, a printout at a remote or attached device, and combinations thereof. The information displayed can include, e.g., the information and instructions related to the presence, concentration and amount of a gas, warnings, alarms and combinations thereof.

In some embodiments, the gas detector includes a window disposed between the infrared radiation source and the sample chamber, between the detectors (e.g., the analytical and/or reference detectors) and the sample chamber, or both. Useful windows are transparent to infrared radiation. A window can be positioned to prevent the gaseous sample from contacting the infrared radiation source. In addition or in the alternative the window can be positioned to prevent the gaseous sample from contacting the analytical and reference detectors. One example of a suitable window is a sapphire window. Typically, if present, an airtight seal is created around the window to prevent the gaseous sample from entering the portion of the gas detector that is to be protected from the gaseous sample including, e.g., the infrared radiation source and the detectors. O-rings and similar sealing means are suitable for that purpose.

The gas detector can optionally include various other components including, e.g., heating elements, beam splitters, beam collimators, lenses (e.g., light focusing lenses and light diffusing lenses), wave guides (which may optionally be heated) and other conventional devices associated with focusing infrared radiation, windows (e.g., frosted windows), and combinations thereof can be included as appropriate. Also useable, if desired, are devices associated with dispersing infrared radiation, diffusing infrared radiation, and combinations thereof including, e.g., diffusing windows (e.g., sapphire windows). While not necessary for the efficient and effective practice of the present invention, when these types of devices are used, it is preferred that they are used in a manner that promotes uniform distribution of infrared radiation incident on the analytical and reference detectors employed.

Other conventional components and methods known to those skilled in the art can be used in conjunction with the gas detector. Such components include, e.g., those components used in commercially available gas detectors including, e.g., the "SEC Millenium" infrared hydrocarbon gas detector sold by Sensor Electronics Corporation, Minneapolis, Minn.

The gas detector can be configured in a variety of shapes and to have various dimensions suitable for their intended use and location of use. While not limited thereto, in one embodiment, the gas detector is cylindrical in shape and includes a number of apertures (e.g., holes, slits, or other openings) in the cylinder wall to allow gas to pass in and out of the detector. The gas detector can have an open configuration in which spacers extending between the portion of the detector that houses the detectors and the portion of the detector that houses the source of radiation. The spacers are dimensioned so as to provide minimal interference with the flow of a gas of interest into and out of the sample chamber. Any suitable material can be used for the components of the device, but materials are preferably selected such that they are inert to the environments to which they will be exposed. Useful materials include, e.g., stainless steel and anodized aluminum.

Although not limited thereto, preferred embodiments of the gas detector are those in which a gaseous sample passes through the gas detector in a continuous and diffusive manner.

In one preferred embodiment, the gas detector monitors gases present in the atmosphere in which the detector is located. The gas detector is well suited for use in a variety of applications and for detecting the presence and/or amount of gas in a variety of locations including, e.g., rooms, sterilization chambers, vacuum chambers, air circulation and recirculation passageways and systems, pipelines, HVAC, air quality applications, vents, industrial equipment, petrochemical applications (e.g., oil rigs), power plants, and various outdoor environments.

For applications that include a flowing gas, the gas detector can be positioned in parallel or in series with a stream of gas. If desired, the sample can be forcibly pushed or pulled through the gas detector using any suitable device including, e.g., mechanical, hydraulic, and air driven devices.

The gas detector is suitable for detecting a variety of gases and vapors including, e.g., gases and vapors that include a carbon hydrogen bond including, e.g., gases and vapors of hydrocarbons (e.g., methane, ethane, propane, butane, 1-butene, hexane, heptane, octane, dimethyl propane, isobutene, ethylene, propylene, benzene, ethyl benzene, xylene, toluene), alcohols (e.g., methanol, ethanol, propanol, and cyclohexanol), clycohexanone, ethylene oxide, carbon dioxide, carbon monoxide, nitrous oxide, water vapor, vapors of other compounds, and combinations thereof.

Figure 4:
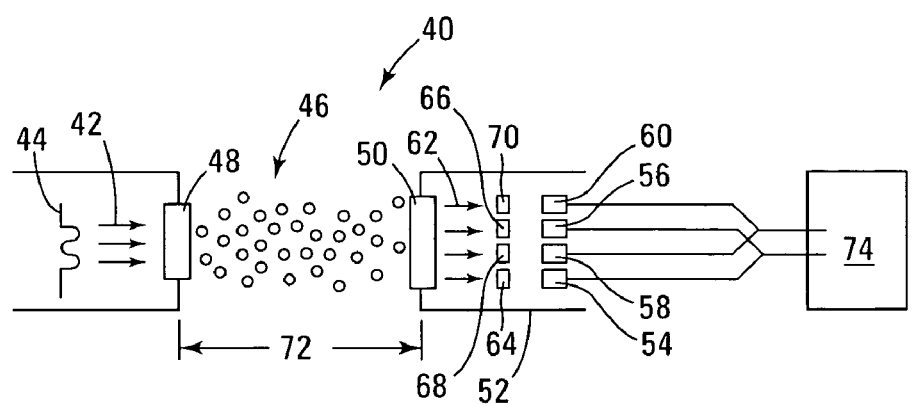
FIG. 4 is a schematic representative of infrared radiation flow taken in a direction transverse to the optical path in the gas detector of FIG. 2.
Figure 2:
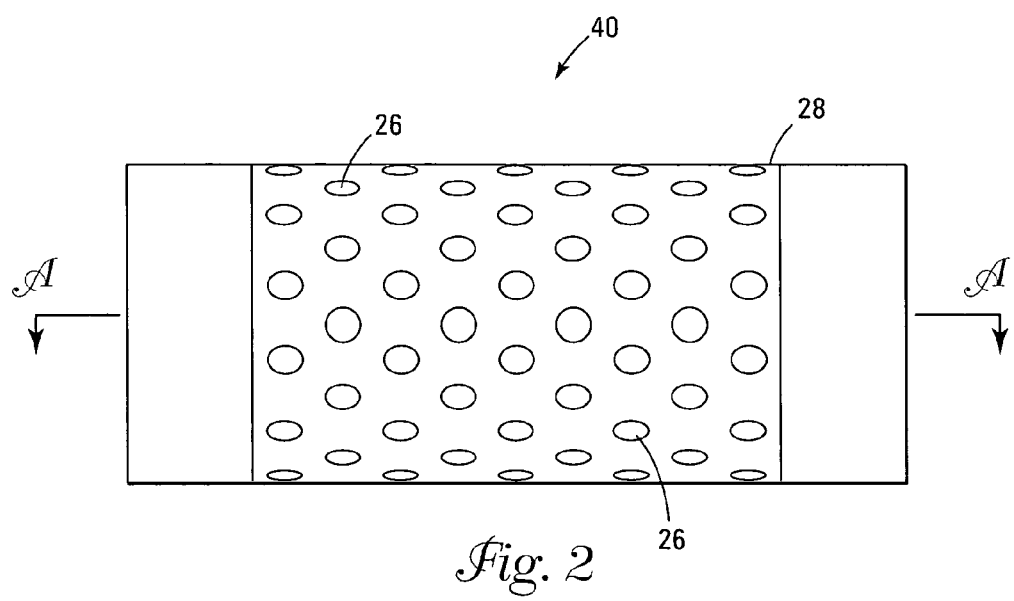
FIG. 2 is a perspective view of a gas detector.
Figure 3:
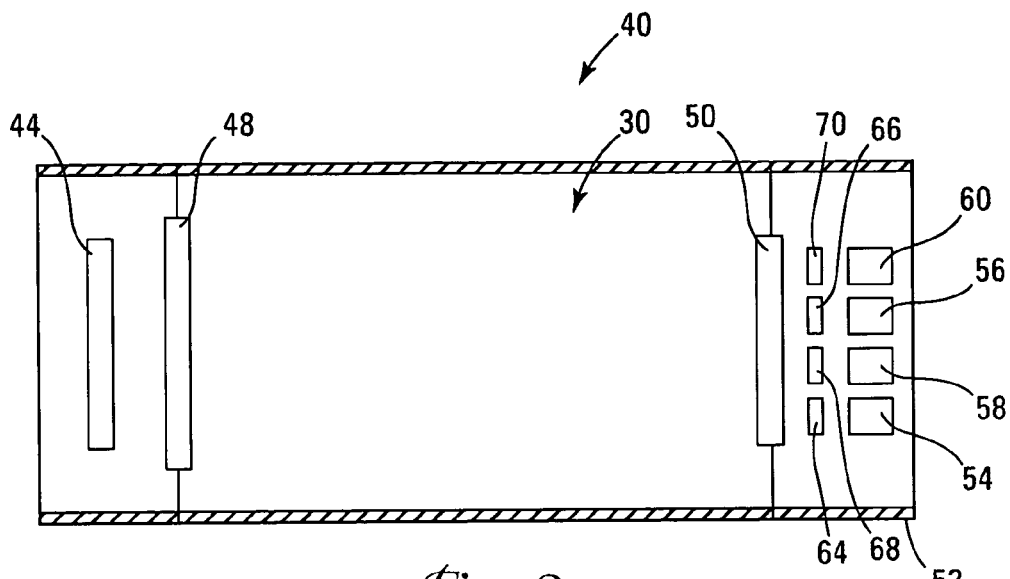
FIG. 3 is a cross sectional view taken along line A—A of FIG. 2

FIGS. 2–4 illustrate one exemplary embodiment of the gas detector 40. The gas detector 40 includes a housing 28 that includes perforations 26 that allow gas molecules to pass into and out of the optical path of the gas detector 40. The gas detector 40 includes a source of infrared radiation 44, a sample chamber 30 through which a gaseous sample 46 containing the gas of interest passes, two analytical detectors 54, 56 for detecting the gas of interest and two reference detectors 58, 60. The optical path 72 extends from the source of infrared radiation 44, through the sample chamber 30 to the detectors 54, 56, 58, 60.

The first analytical detector 54, the second analytical detector 56, the first reference detector 58, and the second reference detector 60 are housed in a receptacle 52. A first set of interference filters 64, 66 is positioned such that the infrared radiation 62 transmitted through the gaseous sample passes through the interference filters 64, 66 before reaching the analytical detectors 54, 56, respectively. The interference filters 64, 66 of the first set of filters transmit infrared radiation of a first predetermined band of wavelengths. The first predetermined band of wavelengths is selected based upon the type of gas that is to be detected by the analytical detectors 54, 56.

A second set of interference filters 68, 70 is positioned such that infrared radiation passes through the interference filters 68, 70 of the second set before reaching the reference detectors 58, 60. The interference filters 68, 70 of the second set of filters transmit infrared radiation of a second predetermined band of wavelengths. The second predetermined band of wavelengths is selected such that radiation at the second predetermined band of wavelengths is not absorbed by the gaseous sample 46 in the sample chamber 30.

In operation, infrared radiation 42 is emitted from the infrared radiation source 44 and passes through a window 48 that is transparent to infrared radiation 42, through the gaseous sample 46 that is present in the sample chamber 30, through another window 50 to the detectors 54, 56, 58, 60. The amount and type (i.e., wavelength) of radiation 42 absorbed by a gas in the gaseous sample 46 depends upon the type of gas in the sample 46 and concentration thereof.

The amount of infrared radiation 42 emitted by the source of radiation 44 is determined and compared to the amount of infrared radiation 62 received by the analytical detectors 54, 56 after having passed through the gaseous sample 46. The determination and comparison can be performed by any suitable processing means including, e.g., a microprocessor 74 or other processing means. The processing means is configured to receive data from the analytical detectors 54, 56 and reference detectors 58, 60.

Other embodiments are within the claims. Although the embodiment of the gas detector illustrated in FIG. 4, for example, utilizes a combination of two analytical detectors and two reference detectors, many other combinations of analytical detectors and reference detectors may be effectively used. Further, although a reference detector is not required, the gas detector can include multiple reference detectors.

Figure 5:
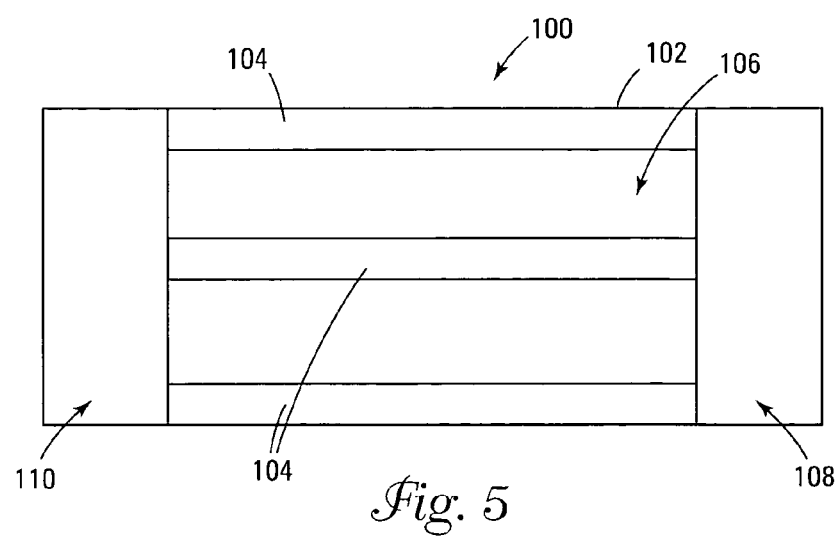
FIG. 5 is a side view of a gas detector according to another embodiment.

In other embodiments, the gas detector 100 is configured to have an open structure 102 that includes spacers 104 that join a component 110 (e.g., a housing) that includes the source of infrared radiation and a component 108 (e.g., a housing) that includes the detectors, an example of which is illustrated in FIG. 5. The length of the spacers 104 is selected to define the desired length of the optical path. The open nature of the housing enables a gaseous sample to pass in and out of the sample chamber 106 with minimal interference from the gas detector housing.

Figure 6:
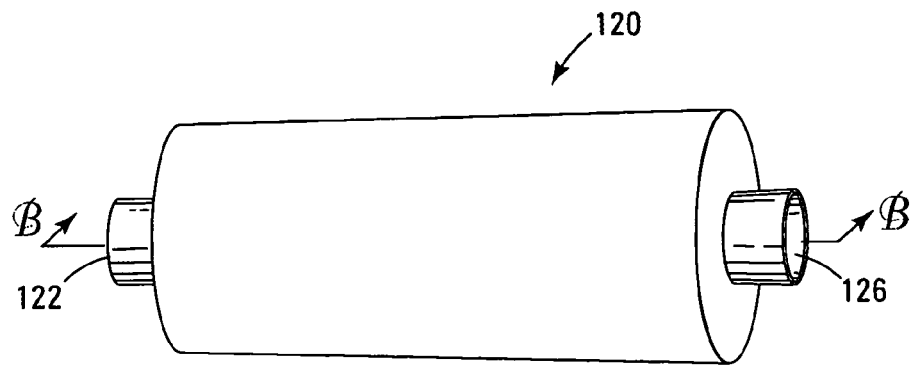
FIG. 6 is a perspective view of a gas detector according to another embodiment.
Figure 7:
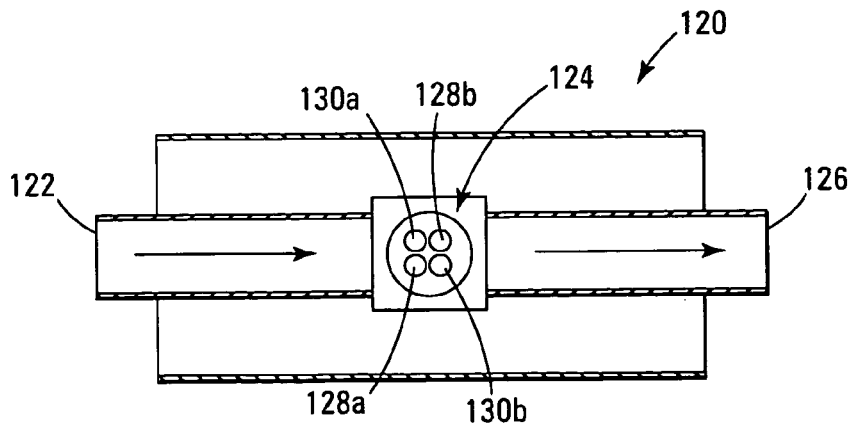
FIG. 7 is a cross sectional view of the gas detector of FIG. 6 taken along line B—B

In another embodiment, the gas detector 120 is configured to detect gas from a stream of gas, as illustrated, for example, in FIG. 6. The gas detector 120 is connected to a continuous stream of gas (not shown) such that a gaseous sample from a stream of gas is directed through inlet 122 into an enclosed infrared radiation gas detector 120, through the sample chamber 124 of the detector 120 and then passed out of the detector through outlet 126. Upon exiting the gas detector, the sample can re-enter the stream of gas from which it was taken or be routed elsewhere, such as through an exhaust system. Infrared radiation from at least one source is passed through the gaseous sample in the sample chamber 124 to the analytical detectors 128a, 128b and reference detectors 130a, 130b.

Figure 8:
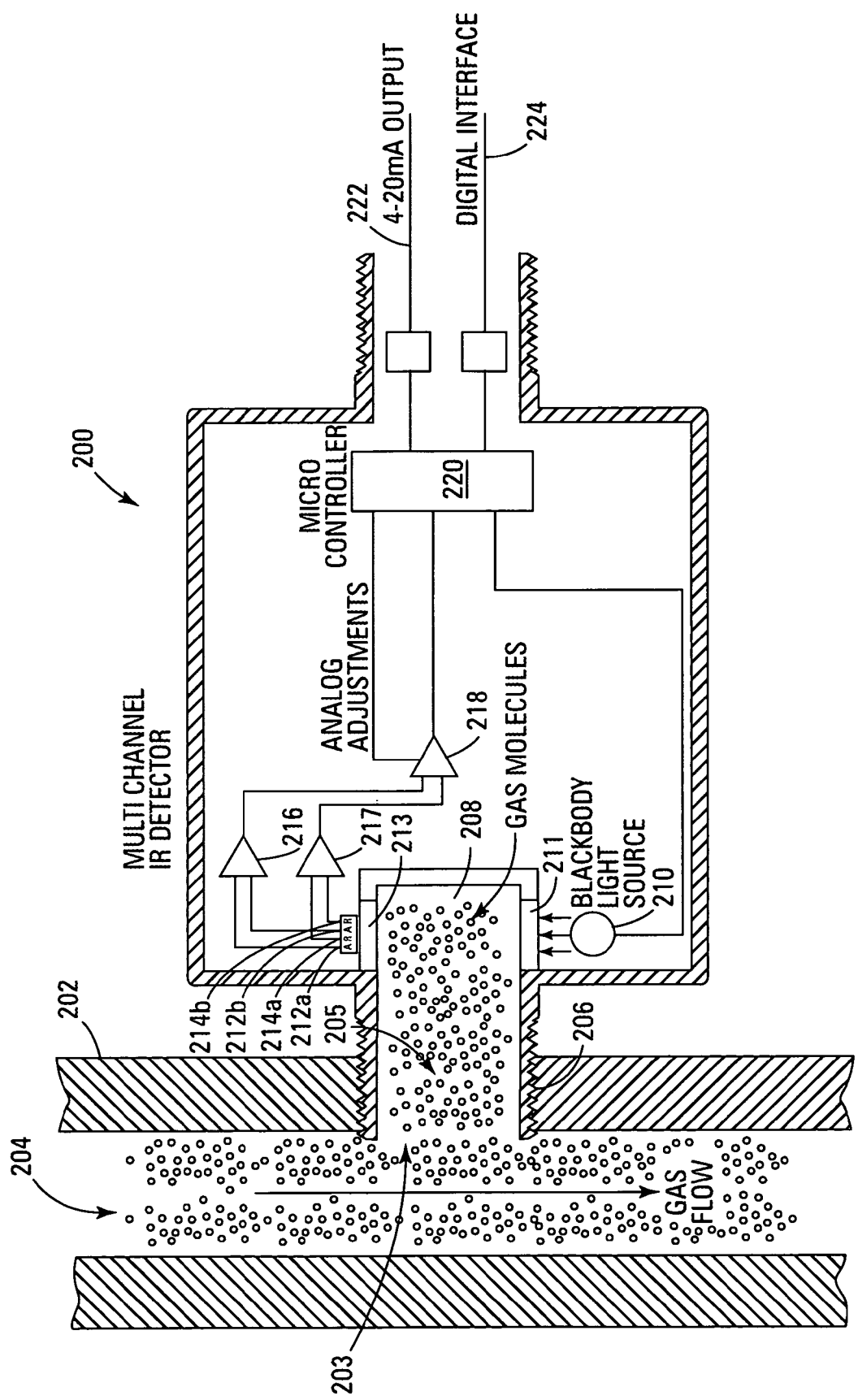
FIG. 8 is a cross sectional view of a gas detector according to another embodiment attached to a pipe.

In another embodiment, the gas detector 200 is in fluid communication with a pipe 202 through which a gas 204 is flowing, as illustrated in FIG. 8. The gas detector 200 is attached to the pipe 202 through a threaded attachment 206. The gas detector 200 includes a passage way 203 for receiving a diffusing gaseous sample 205, a sample chamber 208 through which the optical path passes, a source of infrared radiation 210, which is protected from the gas by a window 211, two analytical detectors 212a, 212b, and two reference detectors 214a, 214b, which are protected from the gas by a window 213, two summing nodes 216, 217, an analog adjustment 218, a microprocessor 220, a output 222 and a digital interface 224. The sample chamber 208 is closed and the gaseous sample 205 flows in and out of the sample chamber through the passage way 203. Summing node 216 sums the signals generated by the analytical detectors 212a and 212b and forwards the summed signals to the microprocessor. Summing node 217 sums the signals generated by the reference detectors 214a and 214b and forwards the summed signals to the microprocessor. Any component or operation (e.g., software) suitable for summing the signals can be used including, e.g., summing nodes (e.g., analog and digital summing nodes), summing amplifiers, microprocessors and combinations thereof. The digital interface 224 allows information to be retrieved from or passed to the detector through any suitable device or component. A controller, or a user through an interface such as a computer, for example, can interrogate the detector, provide information or direction to the detector and retrieve information from the detector through the digital interface 224.

Various modifications and alterations of the invention will become apparent to those skilled in the art without departing from the spirit and scope of the invention, which is defined by the accompanying claims. It should be noted, for example, that steps recited in any method claims below do not necessarily need to be performed in the order that they are recited. Those of ordinary skill in the art will recognize variations in performing the steps from the order in which they are recited. In certain embodiments, for example, steps may be performed simultaneously.

Other embodiments are within the claims. Although the gas detector has been described with respect to radiation in the infrared range of wavelengths, the principals disclosed herein can be applied to gas detectors based on other radiation wavelengths including, e.g., ultraviolet light and visible light. In an embodiment that operates in the ultraviolet wavelength range, the source of radiation provides ultraviolet radiation and the detectors are capable of detecting ultraviolet radiation. The accompanying claims should be construed with these principles in mind.

What is claimed is:

1. A gas detector comprising:
   at least one source of infrared radiation;
   at least two analytical detectors, each analytical detector adapted to provide an output signal indicative of a first gas of interest, said analytical detectors being positioned to receive radiation from said source of radiation, a first of said at least two analytical detectors being positioned to receive radiation of a first predetermined wavelength, and a second of said at least two analytical detectors being positioned to receive radiation of said first predetermined wavelength;
   at least one reference detector adapted to provide an output signal independent of the first gas of interest;
   a means for summing said output signals detected by said at least two analytical detectors; and
   a sample chamber for receiving a gaseous sample,
   an optical path from said source of infrared radiation to said analytical detectors passing through said sample chamber.

2. The gas detector of claim 1, wherein said at least two analytical detectors further comprise said means for summing.

3. The gas detector of claim 1, wherein said means for summing comprising summing amplifier.

4. The gas detector of claim 1, wherein said means for summing comprises a summing node.

5. The gas detector of claim 1, wherein said means for summing comprises an analog summing node.

6. The gas detector of claim 1, wherein said means for summing comprises a digital summing node.

7. The gas detector of claim 1, wherein said means for summing comprises a microprocessor.

8. The gas detector of claim 1, further comprising an interference filter positioned to filter radiation received by at least one of said at least two analytical detectors.

9. The gas detector of claim 1, wherein said at least one source of infrared radiation comprises at least one of heated filament, a black body source, and light emitting diode.

10. The gas detector of claim 1, wherein said at least one source of infrared radiation comprises an incandescent lamp.

11. The gas detector of claim 1, wherein said at least one source of infrared radiation consists of one source of infrared radiation.

12. The gas detector of claim 1 comprising at least three analytical detectors.

13. The gas detector of claim 1 comprising at least four analytical detectors.

14. The gas detector of claim 1 further comprising at least two additional analytical detectors, said at least two additional analytical detectors adapted to provide an output signal indicative of a second gas of interest, the second ass of interest being different from the first gas of interest.

15. The gas detector of claim 14, wherein a filter is interposed between the at least one source of infrared radiation and each additional analytical detector, the filter being adapted to transmit radiation of a second band of wavelengths, said second band of wavelengths corresponding to radiation of a wavelength absorbed by the second gas of interest.

16. The gas detector of claim 14, wherein a filter is interposed between the at least one source of infrared radiation and each reference detector, each filter being adapted to transmit radiation of a third band of wavelengths, the third band of wavelengths corresponding to radiation of wavelength that is not absorbed by the first gas of interest and the second gas of interest.

17. The gas detector of claim 1, wherein a filter is interposed between the at least one source of infrared radiation and each analytical detector, the filter being adapted to transmit infrared radiation of a first band of wavelengths, said first band of wavelengths corresponding to radiation of a wavelength absorbed by the first gas of interest.

18. The gas detector of claim 1, further comprising a microprocessor for receiving and analyzing signals generated by the analytical detectors.

19. The gas detector of claim 1 comprising at least two of said reference detectors.

20. The gas detectors of claim 19, wherein a first one of said at least two reference detectors receives a first predetermined wavelength and a second one of said at least two reference detectors receives said first predetermined wavelength.

21. A gas detector for detecting a predetermined gas, the gas detector comprising:
a source of infrared radiation;
a plurality of infrared radiation detectors, at least two of said infrared radiation detectors being, adapted to detect radiation of a first wavelength and being adapted to provide an output signal corresponding to the presence of the gas of interest; and
a means for summing said output signals generated by said analytical detectors.

22. The gas detector of claim 21, wherein said at least two analytical detectors further comprise said means for summing.

23. The gas detector of claim 21, wherein said means for summing comprises at least one of a summing amplifier, a summing node, an analog summing node, a digital summing node and a microprocessor.

24. The gas detector of claim 21 further comprising an interference filter positioned to filter radiation received by at least one of said at least two analytical detectors.

25. The gas detector of claim 21, wherein said at least one source of infrared radiation comprises at least one of heated filament, a black body source, a light emitting diode, and an incandescent lamp.

26. The gas detector of claim 20, wherein said at least one source of infrared radiation consists of one source of infrared radiation.

27. The gas detector of claim 21 comprising at least three analytical detectors.

28. The gas detector of claim 21 comprising at least four analytical detectors.

29. The gas detector of claim 21 further comprising at least two additional analytical detectors, said at least two additional analytical detectors adapted to provide an output signal indicative of a second gas of interest, the second gas of interest being different from the first gas of interest.

30. The gas detector of clam 29, wherein a filter is interposed between the at least one source of infrared radiation and each additional analytical detector, the filter being adapted to transmit radiation of a second band of wavelengths said second band of wavelengths corresponding to radiation of a wavelength absorbed by the second gas of interest.

31. The gas detector of claim 29, wherein a filter is interposed between the at least one source of infrared radiation and each reference detector, each filter being adapted to transmit radiation of a third band of wavelengths, the third band of wavelengths corresponding to radiation of wavelength that is not absorbed by the first gas of interest and the second gas of interest.

32. The gas detector of claim 21, wherein a filter is interposed between the at least one source of infrared radiation and each analytical detectors, the filter being adapted to transmit infrared radiation of a first band of wavelength, said first band of wavelengths corresponding to radiation of a wavelength absorbed by the first gas of interest.

33. The gas detector of claim 21, further comprising a microprocessor for receiving and analyzing signals generated by the analytical detectors.

34. A method of detecting gas using a gas detector comprising
a source of infrared radiation,
at least two analytical detectors, each of said at least two analytical detectors being adapted to generate a signal indicative of a first gas of interest, a sample chamber, and
an optical path passing through said sample chamber, the method comprising:
transmitting infrared radiation from said source of infrared radiation through a gaseous sample present in the sample chamber of said gas detector;
detecting infrared radiation of a first predetermined wavelength at a first of said at least two analytical detectors;
detecting infrared radiation of said first predetermined wavelength at a second of said at least two analytical detectors;
sending a signal from said analytical detectors to a processor; and summing the signals from said analytical detectors.

35. The method of claim 34, wherein said summing occurs in said analytical detectors.

36. The method of claim 34, wherein said summing occurs in a processor.

37. The method of claim 34, wherein said summing occurs prior to said analytical detectors sending a signal to said processor.

38. The method of claim 34, wherein said summing occurs after said analytical detectors send a signal to said processor.

39. The method of claim 34, wherein radiation from the source of infrared radiation that is incident on the analytical detectors is essentially unreflected from surfaces interposed between the analytical detectors and the source of infrared radiation.

40. A method of analyzing a gaseous sample, the method comprising:
passing the gaseous sample through the sample chamber of a gas detector comprising
at least one source of infrared radiation,
at least two analytical detectors, each analytical detector being adapted to provide an output signal indicative of a first gas of interest, said analytical detectors being positioned to receive radiation from said source of radiation, and
a sample chamber;
radiating the gaseous sample with radiation from said source of infrared radiation;
detecting said radiation of a first predetermined wavelength at a first of said at least two analytical detectors;
detecting said radiation of said first predetermined wavelength at a second of said at least two analytical detectors;
generating signals corresponding to said detected radiation;
summing signals generated by said analytical detectors; and
analyzing the summed signals generated by the detectors.

41. The method of claim 40, wherein the analyzing comprises determining the presence or absence of a first gas of interest in the gaseous sample.

42. The method of claim 40, wherein the analyzing comprises determining the concentration of a first gas of interest in the gaseous sample.

43. The method of claim 40, wherein the analyzing comprises
determining the concentration of the first gas of interest, and
determining the concentration of a second gas of interest.

* * * * *